United States Patent
Hagen et al.

[11] Patent Number: 5,916,218
[45] Date of Patent: Jun. 29, 1999

[54] SAW FOR SURGICAL PURPOSES

[75] Inventors: Thomas Hagen, Neuhausen; Rainer Häusler, Tuttlingen, both of Germany

[73] Assignee: Aesculap AG & Co. KG, Tuttlingen, Germany

[21] Appl. No.: 08/838,690

[22] Filed: Apr. 9, 1997

[30] Foreign Application Priority Data

Apr. 15, 1996 [DE] Germany ............... 196 14 832

[51] Int. Cl.6 .................................. A61B 17/14
[52] U.S. Cl. ................ 606/82; 606/176; 30/337
[58] Field of Search ............... 606/82, 176, 177, 606/167; 30/337, 338, 339, 166.3; 279/9.1

[56] References Cited

U.S. PATENT DOCUMENTS

| 1,577,880 | 3/1926 | Stuart | 30/337 |
| 3,750,283 | 8/1973 | Hoffman | 30/338 |
| 4,922,614 | 5/1990 | Machida | 606/167 |

FOREIGN PATENT DOCUMENTS

| 35 00 445 | 7/1986 | Germany . |
| 36 22 761 | 1/1988 | Germany . |

*Primary Examiner*—Michael H. Thaler
*Attorney, Agent, or Firm*—Barry R. Lipsitz; Ralph F. Hoppin

[57] ABSTRACT

In a saw for surgical purposes comprising a saw blade holder movable by a motor and a saw blade fixable in the saw blade holder, to enable insertion and removal of the saw blade without a tool, it is proposed that the saw blade holder comprise an insert guide for the saw blade with a holdback projection, that the saw blade carry a resilient detent projection which in a relaxed position, with the saw blade inserted in the insert guide, engages the holdback projection from behind, and that an actuating element be mounted on the saw blade holder for displacement against the resilient detent projection, the actuating element moving the resilient detent projection, during the insertion, into a tensioned position in which the detent projection is pushable past the holdback projection when the saw blade is pulled out of the saw blade guide.

16 Claims, 4 Drawing Sheets

SAW FOR SURGICAL PURPOSES

BACKGROUND OF THE INVENTION

The invention relates to a saw for surgical purposes comprising a saw blade holder movable by a motor and a saw blade fixable in the saw blade holder.

With saws of this kind, exchange of the saw blades usually requires opening the saw blade holder with a suitable tool, for example, with a wrench, and closing it again after insertion of another saw blade. This is a time-consuming and complicated operation.

SUMMARY OF THE INVENTION

The object underlying the invention is to so design a generic saw that the insertion and fixing of a saw blade in a saw blade holder and also the removal thereof can be carried out in a simple way without a special tool.

This object is accomplished with a saw of the kind described at the outset in accordance with the invention in that the saw blade holder comprises an insert guide for the saw blade with a holdback projection, in that the saw blade carries a resilient detent projection which in a relaxed position, with the saw blade inserted in the insert guide, engages the holdback projection from behind, and in that an actuating element is mounted on the saw blade holder for displacement against the resilient detent projection, and the actuating element moves the resilient detent projection, during the insertion, into a tensioned position in which the detent projection is pushable past the holdback projection when the saw blade is pulled out of the saw blade guide.

With this saw blade holder, the saw blade is guided and fixed transversely to its longitudinal direction by the insert guide. Fixing in the direction of insertion is effected by the resilient detent projection of the saw blade engaging the holdback projection from behind.

To release this axial fixing it is sufficient to push the actuating element forwards against the resilient detent projection in order to thereby move the detent projection into the tensioned position. It is then readily possible to pull the saw blade forwards out of the saw blade guide again.

It is particularly advantageous for the saw blade to comprise two resilient detent projections which in the relaxed position protrude from the plane of the saw blade towards opposite sides. It is then of no consequence in which position the saw blade is inserted into the saw blade guide.

It is expedient for the insert guide to be designed so as to have no projection on the side facing away from the holdback projection. Thus, one of the two projections is moved permanently into the tensioned position by the insert guide, while only the other detent projection effects the axial fixing in the described manner and is optionally movable by the actuating element into the tensioned position.

In a particularly preferred embodiment of the invention, provision is made for the resilient detent projection or projections to be formed by a spring tongue which is cut out of the saw blade and protrudes in the relaxed position with its free edge from the plane of the saw blade. Such a tongue can simply be punched by punching operations out of the saw blade and bent into a shape in which in the relaxed state it protrudes from the plane of the saw blade.

With detent projections extending in opposite directions, this can be realized by two spring tongues which are bent out of the plane of the saw blade towards opposite sides.

In a preferred embodiment provision is made for the actuating element to be a push button which is pushable adjacent to the holdback projection transversely to the plane of the insert guide into the insert guide.

This push button can simply be pushed in manually from the outside, however, in accordance with a particularly preferred embodiment, provision is made for the saw blade holder to carry an eccentric element which is rotatable about the longitudinal axis of the saw blade holder and rests with a bearing surface which is eccentric in relation to the axis of rotation against the actuating element. By turning the eccentric element on the saw blade guide, the actuating element can thereby be activated and moved against the resilient detent projection, which causes the saw blade to be released. A particular advantage of this construction is that the actuating element is pressed resiliently against the eccentric bearing surface by the resiliently pushed in detent projection, and this, in turn, results in the eccentric element maintaining the angular position reached, i.e., the actuating element resting against the eccentric bearing surface of the eccentric element acts as rotary brake for the eccentric element. This makes it possible to rotate the eccentric element for release of the saw blade and to subsequently pull out the saw blade with only one hand. For, the operator can turn the eccentric element to the release position in which it remains on account of the described braking effect. It is, therefore, not necessary to continue holding the eccentric element, and so the operator can take his hand away from the eccentric element, grip the saw blade and pull it out of the saw blade holder. Therefore, not only can the saw blade be released and pulled out without a tool, but even with one hand.

Provision may be made for there to be stops between eccentric element and saw blade holder for delimiting their relative angles of rotation.

These stops are preferably formed by the end surfaces of a circumferential groove which extends on the eccentric element or on the saw blade holder over a certain circumferential angular range and into which a projection fixed on the respective other part protrudes. In particular, this projection can be a ball.

Further provision may be made for the eccentric element to be acted upon by a spring to move it into the angular position in which the actuating element does not move the detent projection into the tensioned position. This ensures that when a saw blade is introduced, it is immediately locked in the axial direction once the full insertion depth is reached, as the actuating element can readily be moved into the pushed out position by the corresponding position of the eccentric element. It is, however, expedient for the spring force of the spring displacing the eccentric element into the release position to be only so large that when the release position of the saw blade is reached in the described manner, the eccentric element remains in this release position on account of the braking effect of the actuating element. Once the saw blade is then pulled out, the resilient force of the detent projection is eliminated and so the actuating element is then also no longer pressed against the eccentric bearing surface of the eccentric element. Once this is the case, the spring force of the spring is sufficient to turn the eccentric element into the initial position, i.e., the lock position, again.

It is expedient for a rotary spring which surrounds the saw blade holder and causes this return of the eccentric element to the lock position to adjoin the eccentric element.

In a preferred embodiment provision may be made for the saw blade holder to carry a sleeve which surrounds the saw blade holder, with the eccentric element being rotatably mounted on the sleeve and resting against an annular shoulder, for the sleeve to have a window-like opening for the actuating element to pass therethrough, with the opening being covered by the bearing surface of the eccentric element, and for a further annular shoulder to be provided on the sleeve for axially fixing the eccentric element between itself and the other annular shoulder.

It is also expedient for the further annular shoulder to be a bushing which is pushable onto the sleeve and forms between itself and the sleeve an annular space in which the helical-type rotary spring is arranged.

The bushing and the sleeve can be attached to the saw blade holder by attachment means, for example, screws, which extend jointly through the bushing and the sleeve.

In a preferred embodiment provision is made for the contacting surface between actuating element and bearing surface of the eccentric element to be in the form of a friction surface owing to a suitable choice of material. This design as friction or braking surface causes the frictional connection between the bearing surface and the actuating element pressed by the detent projection of the saw blade against the bearing surface to be increased, and so even with a relatively strong spring turning the eccentric element into the lock position, the eccentric element remains in the release position so long as the saw blade is still in the saw blade holder.

The following description of preferred embodiments of the invention serves in conjunction with the drawings to explain the invention in greater detail.

DETAILED DESCRIPTION OF THE INVENTION

Figure 1:
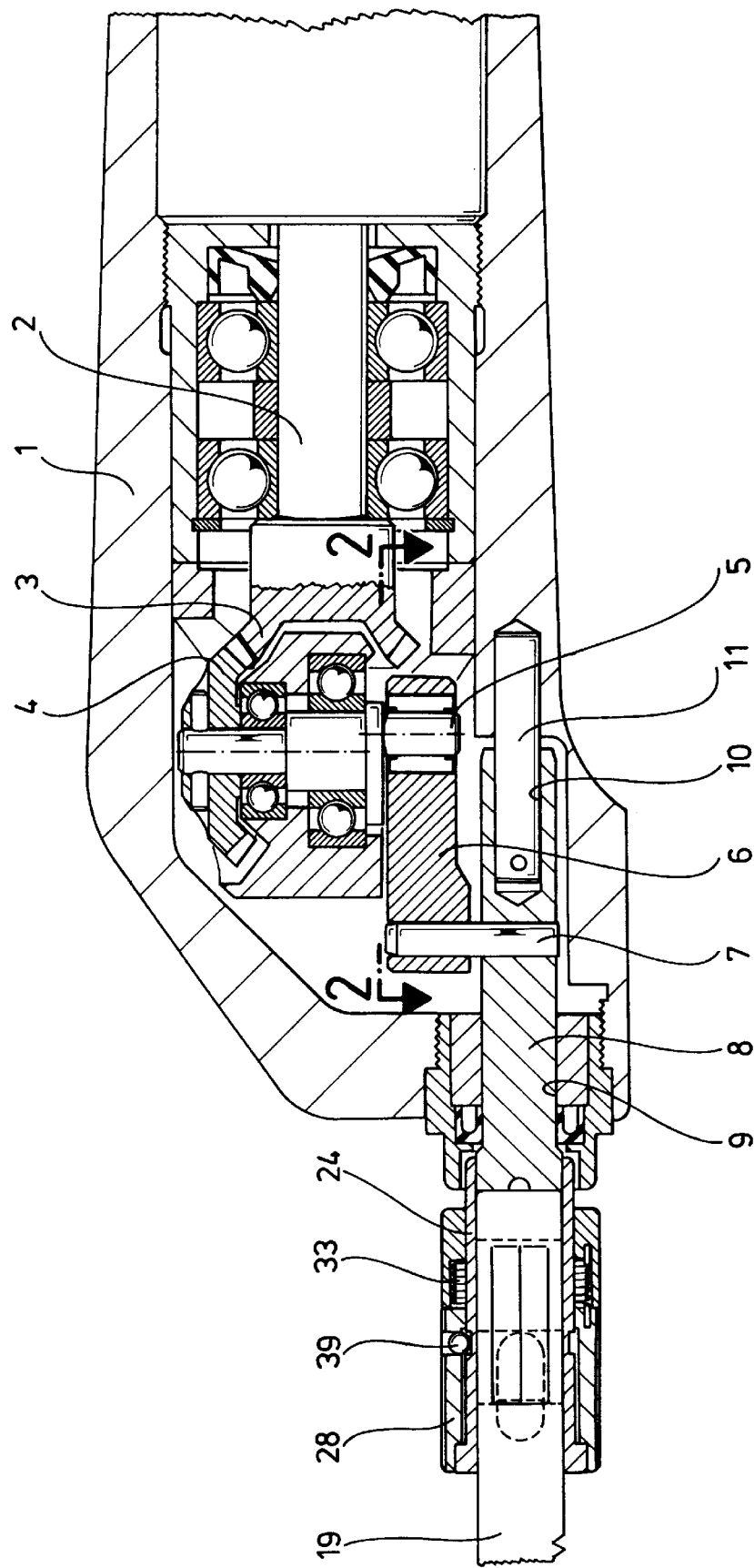
FIG. 1 a longitudinal sectional view of a surgical saw.
Figure 2:
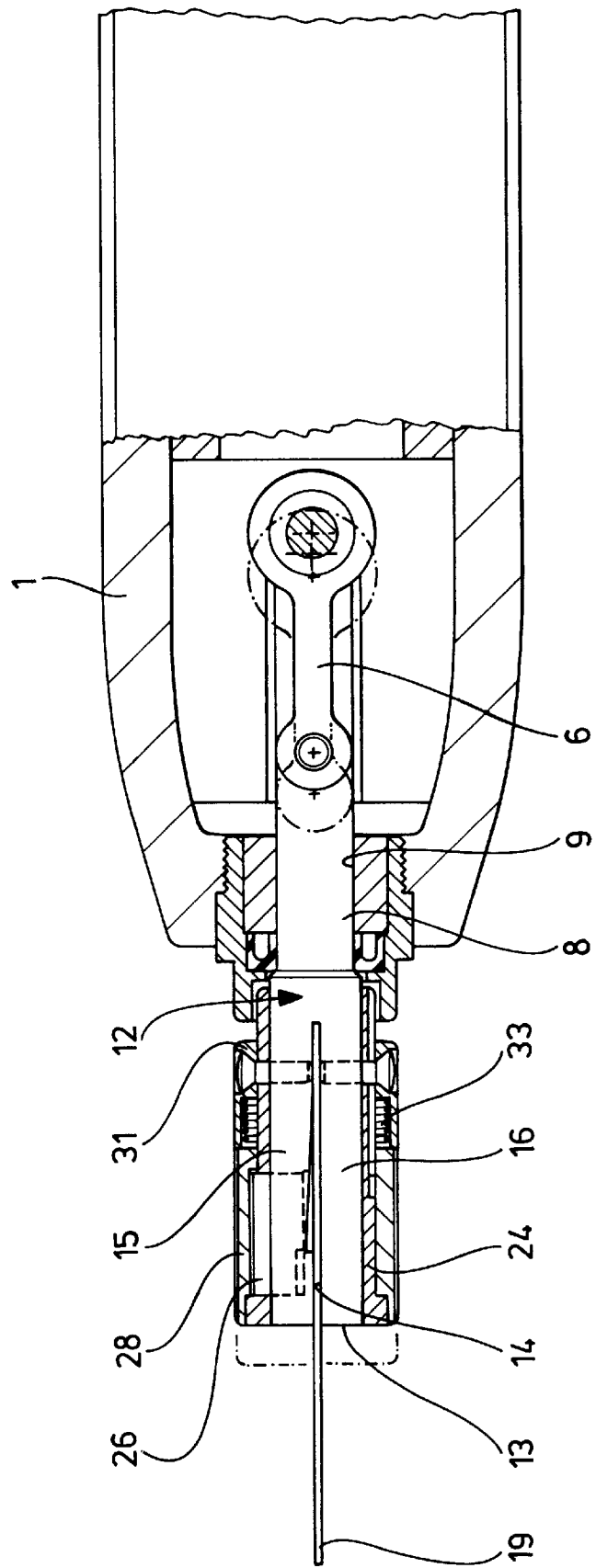
FIG. 2 a sectional view along line 2—2 in FIG. 1.
Figure 3:
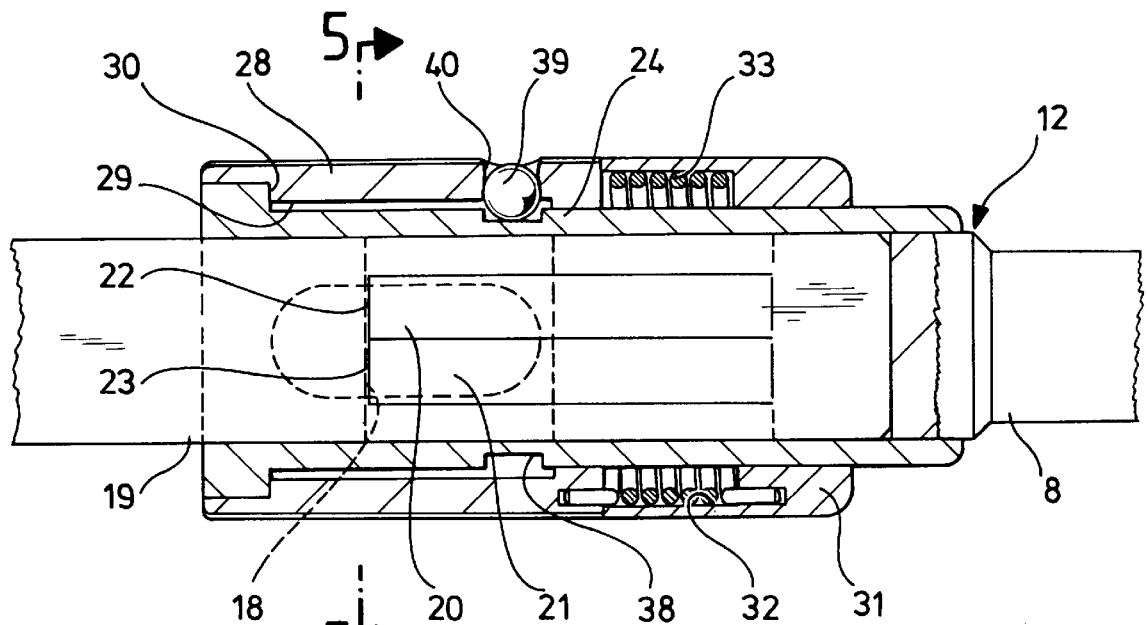
FIG. 3 a longitudinal sectional view of the saw blade holder in accordance with the illustration in FIG. 1.
Figure 4:
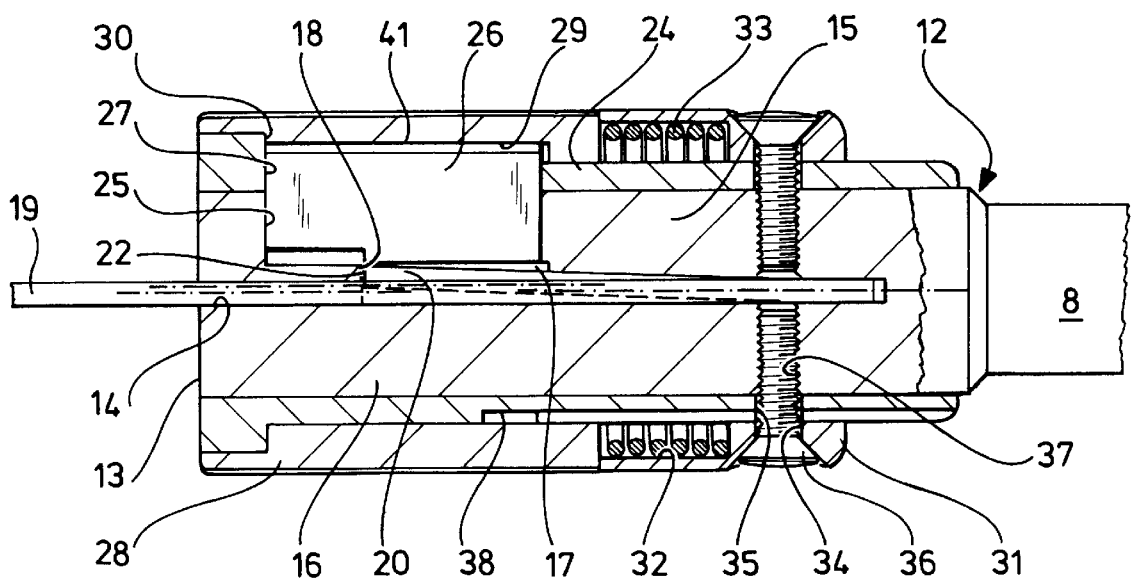
FIG. 4 a longitudinal sectional view of the saw blade holder in accordance with the illustration in FIG. 2.
Figure 5:
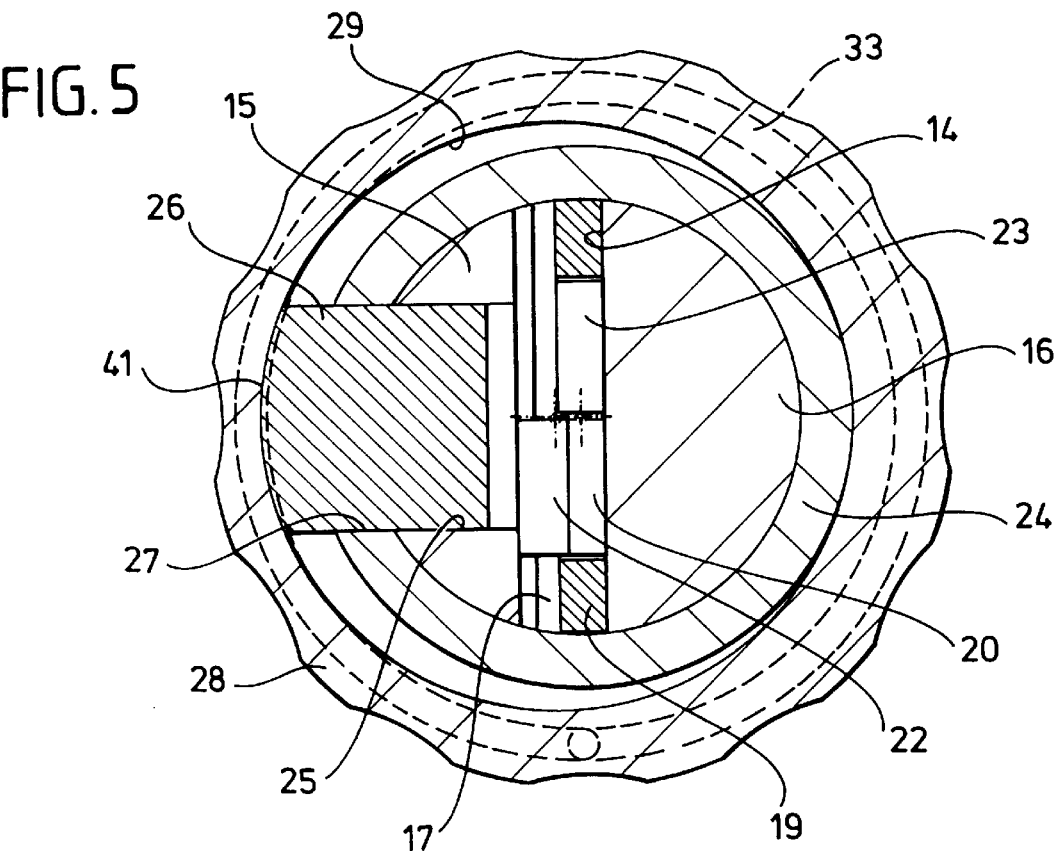
FIG. 5 a sectional view along line 5—5 in FIG. 3 with the actuating element in the lock position.
Figure 6:
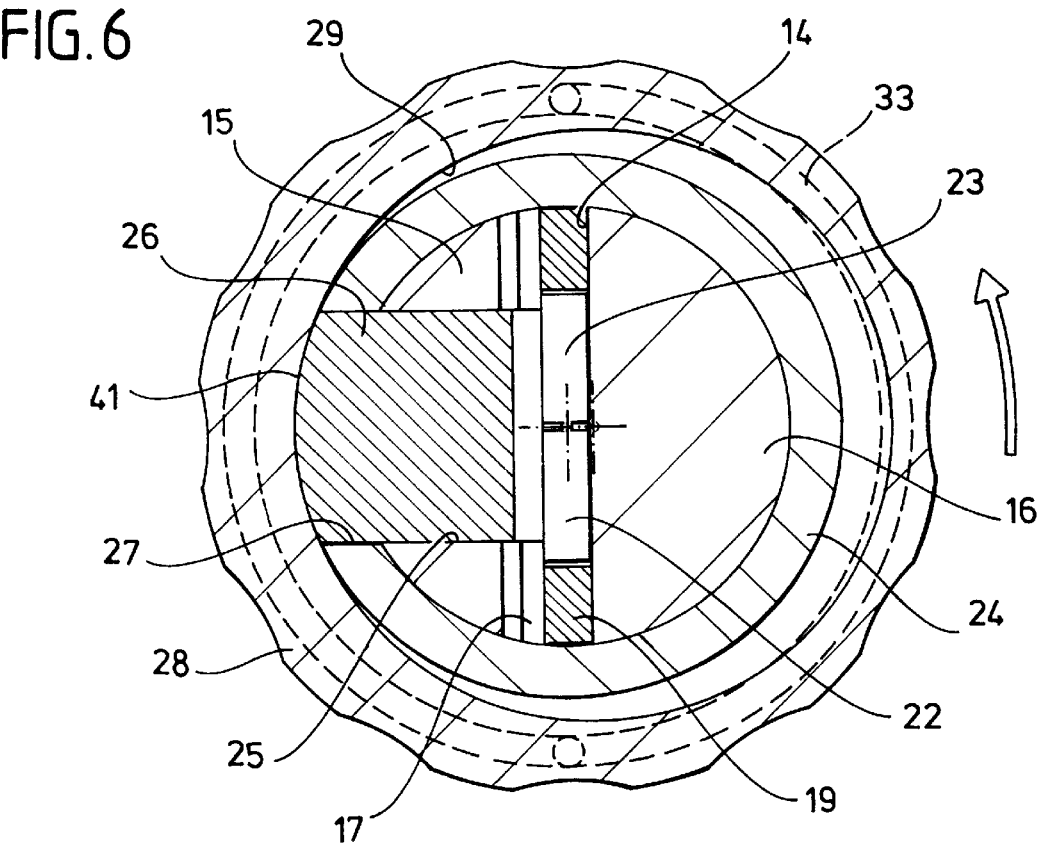
FIG. 6 a view similar to FIG. 5 with the actuating element in the release position.

The saw illustrated in the drawings comprises a housing 1 accommodating an electric motor with a motor shaft 2 arranged in the longitudinal direction of the housing. The motor shaft 2 drives an eccentric 5 via two bevel gears 3, 4. The eccentric 5 transmits its circular movement via a connecting rod 6 to a driver pin 7 which, in turn, is secured in a tool holder 8. The tool holder 8 is mounted for longitudinal displacement in a guide 9 of the housing 1. In addition, a further guide pin 11 mounted on the housing 1 engages a blind hole bore 10 of the tool holder 8. The rotational movement of the motor shaft 2 is converted by the gear means mentioned above into a reciprocating movement of the tool holder 8. The tool holder 8 is thus pushed back and forth periodically in the longitudinal direction of the housing 1.

The tool holder 8 terminates at its free end in a circular-cylindrical saw blade holder 12 which is divided by a central slot 14, introduced from the front end face 13, into two halves 15 and 16, each having an essentially semicircular cross section.

The lower half 16 is of essentially solid construction. However, the upper half 15 has a recess 17 at the side. The depth of the recess 17 increases continuously from the slot 14, starting from the housing, to the free end of the saw blade holder 12. At its end facing away from the housing, the recess 17 continues via a holdback edge 18 into the slot 14.

The slot 14 forms an insert guide for a flat saw blade 19 which is insertable with its rearward end into this slot 14, thereby contacting the upper side and the lower side of the slot 14. Two adjacent spring tongues 20, 21 are punched out of the rearward end of the saw blade 19 that is pushed into the slot 14. The spring tongues 20, 21 are bent out of the plane of the saw blade 19 towards opposite sides so that in the relaxed position these tongues 20, 21 project from the plane of the saw blade 19 with their free edges 22, 23 pointing towards the end face 13 of the saw blade holder 12.

When the saw blade 19 is pushed into the slot 14, the tongue 21 springing out in the downward direction slides along the lower half 16 and is thereby bent into the tensioned position in which this tongue 21 lies in the plane of the saw blade 19.

Initially, the upper tongue 20 is likewise held by the part of the slot 14 adjacent to the end face 13 in the tensioned position, but it can spring out sideways once its edge 22 has passed the holdback edge 18. The upper tongue 20 can then resiliently enter the recess 17 and remains there on account of the spring force of the tongue 20. The dimensions are chosen such that the tongue 20 does not spring out until the saw blade 19 has reached the full insert depth, i.e., the saw blade 19 is fixed in the axial direction by the springing out tongue 20.

The saw blade 19 is fixed transversely to the extent of the slot 14 by a sleeve 24 which is pushed onto the two halves 15, 16 of the saw blade holder 12 and which delimits the slot 14 sideways. The width of the saw blade 19 in this area corresponds to the width of the slot 14.

The upper half 15 of the saw blade holder 12 contains a radial shaft-type opening 25 which extends into the recess 17. Mounted in this opening 25 for displacement transversely to the saw blade 19 is a contacting element 26 which passes through a window-like opening 27 in the sleeve 24.

Mounted concentrically for rotation on the sleeve 24 is a further sleeve 28 with an inner bearing surface 29 which is eccentric in relation to the axis of rotation. This bearing surface 29 covers the window-like opening 27 and the contacting element 26 passing through this opening.

The sleeve 28 is fixed in the axial direction on the sleeve 24, on the one hand, by an annular shoulder 30 formed thereon adjacent to the end face 13 and, on the other hand, by a bushing 31 pushed onto the sleeve 24. The bushing 31 forms between itself and the sleeve 24 an annular space 32 with a helical spring 33 surrounding the sleeve 24 arranged therein. At one end thereof, the helical spring 33 engages the sleeve 28 and at the other end thereof the bushing 31 and so a restoring force is generated when the sleeve 28 is rotated relative to the bushing 31. The bushing 31 and the sleeve 24 have insert openings 34, 35 in alignment with each other through which there are inserted attachment screws 36 which, in turn, are screwed into threaded bores 37 in the upper half 15 and the lower half 16, respectively, of the saw blade holder 12. The bushing 31, the sleeve 24 and the saw blade holder 12 are permanently connected to one another by these attachment screws 36.

The sleeve 24 has on its side opposite the contacting element 26 a circumferential groove 38 which extends over a limited circumferential angle, for example, over 180°. A ball 39 projects into this circumferential groove 38. The ball 39 is, in turn, held in a bore 40 of the sleeve 28 in such a way that it cannot become detached. To this end, the bore 40 can, for example, be caulked on the outside thereof after insertion of the ball 39.

When the sleeve 28 is turned relative to the sleeve 24, the ball 39 runs in the circumferential groove 38 and strikes the end of the circumferential groove 38 at the end faces thereof, which thereby constitutes a delimitation of the angle of rotation of the sleeve 28 relative to the sleeve 24.

The bearing surface 29 and the counter surface 41 of the contacting element 26 resting against it can be designed by a suitable choice of materials as friction or braking surfaces, i.e., as surfaces which have a high friction relative to each other.

If a saw blade is not inserted in the saw blade holder 12, the contacting element 26 can project into the recess 17 and rests against the bearing surface 29 in a non-braking or non-rubbing manner. The sleeve 28 can thereby be turned under the action of the helical spring 33 into the initial position in which the bearing surface 29 is displaced furthest in the radial outward direction relative to the contacting element 26. This position is to be designated the lock position, as the contacting element 26 can be pushed radially outwardly in this position and thereby releases the recess 17.

Therefore, when a saw blade 19 is pushed in, the upper spring tongue 20 can spring into the recess 17 and thereby axially fix the saw blade 19 in the described manner.

When the saw blade 19 is to be removed, the sleeve 28 is turned against the force of the helical spring 33, which causes the eccentric bearing surface 29 to press the contacting element 26 into the recess 17 and thereby bend the upper spring tongue 20 back into the plane of the saw blade 19. When the end position of the sleeve 28 is reached, which is to be designated the release position, the contacting element 26 is pressed with force against the bearing surface 29 by the spring tongue 20, and this results in frictional connection between the bearing surface 29 and the counter surface 41 of the contacting element 26. This frictional connection prevents the sleeve 28 from being turned under the action of the helical spring 33 into the lock position again, and the sleeve 28 remains in the release position even if the operator releases the sleeve 28.

Therefore, with the same hand with which the sleeve 28 has been adjusted, the operator can grip the saw blade 19 after the adjustment and pull it out in the forward direction. Once the front edge 22 of the upper spring tongue 20 passes the holdback edge 18, the resilient contact of the counter surface 41 with the eccentric bearing surface 29 is terminated, and the restoring force of the helical spring 33 is then sufficient to turn the sleeve 28 into the lock position again, in which it then remains.

After complete removal of the saw blade 19, another saw blade can be pushed into the saw blade holder 12 in the described manner.

What is claimed is:

1. A saw for surgical purposes, comprising:

a saw blade holder movable by a motor and a saw blade fixable in said saw blade holder, said saw blade holder comprising an insert guide for said saw blade and a holdback projection, said saw blade carrying at least one resilient detent projection having a relaxed position in which said resilient detent projection protrudes from a plane of said saw blade, and a tensioned position, wherein, in said relaxed position, when said saw blade is inserted in said insert guide, said resilient detent projection engages said holdback projection from behind to secure said saw blade in said saw blade guide, wherein, said resilient detent projection is pushable past said holdback projection into said second position to allow said saw blade to be pulled out of said saw blade guide, and an actuating element mounted on said saw blade holder for displacement between an inactive position and an active position, wherein, in said inactive position, said actuating element allows not tension said resilient detent projection, thereby allows said resilient detent projection to remain in said relaxed position, and in said active position, said actuating element acts against said resilient detent projection to displace said resilient detent projection from the relaxed position, into the second position.

2. A saw as defined in claim 1, wherein:

said saw blade comprises two resilient detent projections which in the relaxed position protrude from said plane of said saw blade towards opposite sides.

3. A saw as defined in claim 2, wherein:

said insert guide is designed so as to not have said resilient detect projection on the side facing away from said holdback projection.

4. A saw as defined in claim 1, wherein:

said at least one resilient detent projection is formed by a spring tongue cut out of said saw blade, and said tongue protrudes in the relaxed position with a free edge thereof from said plane of said saw blade.

5. A saw as defined in claim 1, wherein:

said actuating element comprises a push button which is displaceable adjacent to said holdback projection transversely to said plane of said insert guide.

6. A saw as defined in claim 1, wherein:

said saw blade holder carries an eccentric element which is rotatable about a longitudinal axis of said saw blade holder and rests with a bearing surface, which is eccentric in relation to the axis of rotation, against said actuating element.

7. A saw as defined in claim 6, wherein:

said eccentric element comprises a sleeve surrounding said saw blade holder, and an inner surface of said sleeve comprises the eccentric bearing surface.

8. A saw as defined in claim 7, further comprising:

stops provided between said eccentric element and said saw blade holder for delimiting a relative angle of rotation of said eccentric element with respect to said saw blade holder.

9. A saw as defined in claim 8, wherein:

said stops are formed by end surfaces of a circumferential groove which extends on said eccentric element or on said saw blade holder over a certain circumferential angular range, and a protruding projection fixed on the respective other part protrudes into said groove.

10. A saw as defined in claim 9, wherein:

said protruding projection comprises a ball.

11. A saw as defined in claim 6, wherein:

said eccentric element is acted upon by a spring to move it into the angular position in which said actuating element is in its inactive position.

12. A saw as defined in claim 11, further comprising:

a rotary spring surrounding said saw blade holder and adjoining said eccentric element.

13. A saw as defined in claim 6, wherein:

said saw blade holder carries a sleeve surrounding said saw blade holder, said eccentric element is rotatably mounted on said sleeve and rests against an annular shoulder, said sleeve has a window-like opening for said actuating element to pass therethrough, said opening is covered by said bearing surface of said eccentric element, and a further annular shoulder is provided on said sleeve for axially fixing said eccentric element between itself and said other annular shoulder.

14. A saw as defined in claim 13, wherein:

said further annular shoulder comprises a bushing which is pushable onto said sleeve and forms between itself and said sleeve an annular space in which a helical-type rotary spring is arranged.

15. A saw as defined in claim 14, wherein:

said bushing and said sleeve are attached to said saw blade holder by attachment means extending jointly through said bushing and said sleeve.

16. A saw as defined in claim 6, wherein:

a contacting surface between said actuating element and said bearing surface of said eccentric element is in the form of a friction surface.

\* \* \* \* \*

UNITED STATES PATENT AND TRADEMARK OFFICE
CERTIFICATE OF CORRECTION

PATENT NO. : 5,916,218
DATED : June 29, 1999
INVENTOR(S) : Hagen et al.

It is certified that error appears in the above-identified patent and that said Letters Patent is hereby corrected as shown below:

Column 5, line 62: --first-- is inserted before "relaxed".
Column 5, line 63: "tensioned" is changed to --second--.
Column 6, lines 11 and 12: "allows not tension said resilient detent projection, thereby" is deleted.

Signed and Sealed this

Sixteenth Day of November, 1999

Q. TODD DICKINSON

*Attest:*

*Attesting Officer*     *Acting Commissioner of Patents and Trademarks*